(12) United States Patent
Chung et al.

(10) Patent No.: US 8,689,398 B2
(45) Date of Patent: Apr. 8, 2014

(54) CLEANING APPARATUS AND DETECTING METHOD THEREOF

(75) Inventors: Yu-Liang Chung, Taipei (TW);
Tung-Chuan Wu, Hsinchu (TW);
Chun-Chieh Wang, Banqiao (TW);
Long-Der Chen, Hsinchu (TW)

(73) Assignee: Industrial Technology Research Institute (TW)

( * ) Notice: Subject to any disclaimer, the term of this patent is extended or adjusted under 35 U.S.C. 154(b) by 0 days.

(21) Appl. No.: 13/562,604

(22) Filed: Jul. 31, 2012

(65) Prior Publication Data

US 2012/0291812 A1 Nov. 22, 2012

Related U.S. Application Data

(62) Division of application No. 12/782,111, filed on May 18, 2010, now abandoned.

(30) Foreign Application Priority Data

May 21, 2009 (TW) .............................. 98116839 A (51) Int. Cl.
*A47L 7/04* (2006.01)
*B08B 5/00* (2006.01)

(52) U.S. Cl.
USPC .......................................................... 15/339

(58) Field of Classification Search
USPC ....................... 15/319, 339; 318/587; 324/649
See application file for complete search history.

(56) References Cited

U.S. PATENT DOCUMENTS

| | | | |
|---|---|---|---|
| 4,601,082 A | 7/1986 | Kurz | |
| 4,733,430 A | 3/1988 | Westergren | |
| 4,733,431 A | 3/1988 | Martin | |
| 4,937,912 A * | 7/1990 | Kurz | 15/339 |
| 5,105,502 A | 4/1992 | Takashima | |
| 5,136,750 A | 8/1992 | Takashima et al. | |
| 5,163,202 A * | 11/1992 | Kawakami et al. | 15/319 |
| 5,323,483 A | 6/1994 | Baeg | |
| 5,440,216 A * | 8/1995 | Kim | 318/587 |
| 5,507,067 A | 4/1996 | Hoekstra et al. | |
| 5,608,944 A | 3/1997 | Gordon | |

(Continued)

FOREIGN PATENT DOCUMENTS

| | | |
|---|---|---|
| CN | 1857150 | 11/2006 |
| CN | 101301181 | 11/2008 |

(Continued)

OTHER PUBLICATIONS

OA from corresponding application No. TW 98116839.

(Continued)

*Primary Examiner* — Robert Scruggs
(74) *Attorney, Agent, or Firm* — Lowe Hauptman & Ham, LLP (57) ABSTRACT

The disclosure provides a cleaning apparatus and detecting method thereof. The cleaning apparatus includes a fan, a motor, a detecting device and a control unit. The motor drives the fan to create an air flow through the cleaning apparatus. The detecting device is electrically connected to the motor, and is utilized detected an impedance of the motor. The control unit is electrically connected to the motor and the detecting device respectively, for comparing the impedance of the motor with a predetermined value and outputting a signal indicative of a comparison result.

9 Claims, 12 Drawing Sheets

(56) References Cited

U.S. PATENT DOCUMENTS

| | | |
|---|---|---|
| 5,815,884 A | 10/1998 | Imamura et al. |
| 6,023,814 A * | 2/2000 | Imamura .................. 15/339 |
| 6,571,422 B1 | 6/2003 | Gordon et al. |
| 7,288,912 B2 | 10/2007 | Landry et al. |
| 2005/0278888 A1* | 12/2005 | Reindle et al. .................. 15/319 |
| 2007/0151068 A1* | 7/2007 | Zahuranec et al. ............. 15/319 |
| 2007/0283521 A1 | 12/2007 | Foster et al. |
| 2008/0245810 A1* | 10/2008 | Karwacki et al. ............... 221/13 |

FOREIGN PATENT DOCUMENTS

| | | |
|---|---|---|
| EP | 0 347 223 | 12/1989 |
| JP | 1214326 | 8/1989 |
| TW | 200913955 | 4/2009 |

OTHER PUBLICATIONS

OA from corresponding application No. TW 100145287.

OA from corresponding U.S. Appl. No. 12/782,111.

OA dated Mar. 27, 2012 from corresponding application No. CN 200910171940.6.

\* cited by examiner

CLEANING APPARATUS AND DETECTING
METHOD THEREOF

CROSS REFERENCE TO RELATED
APPLICATIONS

This application is a Divisional of pending U.S. patent application Ser. No. 12/782,111, filed May 18, 2010 and entitled "cleaning apparatus and detecting method thereof", which claims priority of Taiwan Patent Application No. 098116839, filed on May 21, 2009, the entirety of which is incorporated by reference herein.

BACKGROUND OF THE INVENTION

1. Field of the Invention

The disclosure relates to cleaning apparatus and detecting method, and in particular relates to an auto-cleaning device and detecting method.

2. Description of the Related Art

Particles detection technology is currently being used in traditional vacuum cleaners, air cleaners, self-propelled vacuum cleaners, and clean rooms. The detection of amount of particles and environmental control is to make cleaning more efficient. With a simple and effective way to measure the amount of dust and the size, the cleaning performed by the traditional vacuum cleaners, air cleaners, or self-propelled vacuum cleaners can be more efficient, and thus it can promote environment protection by energy-saving and carbon emission reduction.

Known particle detection technology can be broadly divided into the following three categories:
(1) Optical detection: The main principle is to use a pair of optical transmitter and receiver devices, where each receiver detects intensity of light emitted by the corresponding optical transmitter. In principle, the detected intensity increases when the density of dust grains declines, thereby identifying the amount of dust present. For example, in U.S. Pat. No. 4,601,082, optical sensors are used to detect dust. Further, in U.S. Pat. No. 5,608,944 and U.S. Pat. No. 6,571,422, circuits of signal processing, such as amplification, filtering, and other methods, are introduced to improve the sensor's sensitivity.
(2) Pressure-Difference detection: The principle determines whether the filter needs to be replaced or the amount of waste dust collection box is full by comparing the pressure difference between the dust collection box and the suction inlet.
(3) Piezoelectric pressure sensing: The PZT (Lead Zirconate Titanate) pressure sensing element is placed at the inner wall of the vacuum suction inlet. The amount of dust inhaled is determined by the pressures applied to the PZT pressure sensing element by the impact of dust.

BRIEF SUMMARY OF THE INVENTION

In an embodiment, the cleaning apparatus includes a fan, a motor, a detecting device, and a control unit. The motor is for driving the fan to create an air flow through the cleaning apparatus; the detecting device is electrically connected to the motor to detect an impedance of the motor; and the control unit is electrically connected to the detecting device, for comparing the impedance of the motor with a predetermined value and outputting a signal indicative of a comparison result.

In another embodiment, the cleaning apparatus further includes a dust collecting unit positioned in a path of the air flow to trap dust from the air, and the signal indicates a state of the dust collecting unit or filter.

In another embodiment, the cleaning apparatus further includes a blowing device for directing exhaust air of the fan to a sensing surface of the at least one optical sensor.

In another embodiment, a method for debris detection in a cleaning apparatus includes measuring an impedance of a motor of a fan of the cleaning apparatus; determining a level of debris accumulation in the cleaning apparatus based on the impedance of the motor; and issuing a signal indicative of the level of debris accumulation exceeding a predetermined value.

In another embodiment, a method for debris detection in a cleaning apparatus includes arranging multiple optical sensors at different locations in the inlet for detecting the sensing surface at said different locations. The cleaning operation of the cleaning apparatus is controlled based on the determined dust covered surface areas received from said optical sensors.

While the disclosure has been described by way of example and in terms of the preferred embodiments, it is to be understood that the invention is not limited to the disclosed embodiments.

BRIEF DESCRIPTION OF THE DRAWINGS

The present invention can be more fully understood by reading the subsequent detailed description and examples with references made to the accompanying drawings, wherein:

FIG. 1b is an explosive view of a cleaning apparatus according to the embodiment depicted in FIG. 1a;

FIG. 3b is a function diagram of the band pass filter according to the embodiment depicted in FIG. 3a;

DETAILED DESCRIPTION OF THE INVENTION

The descriptions below are made to illustrate exemplary embodiments of the disclosure. It is noted that the drawings of the disclosure are not to scale. The drawings are intended to depict only typical aspects of the disclosure, and therefore should not be considered as limiting the scope of the disclosure. In the drawings, like numbering represents like elements between the drawings.

Figure 1A:
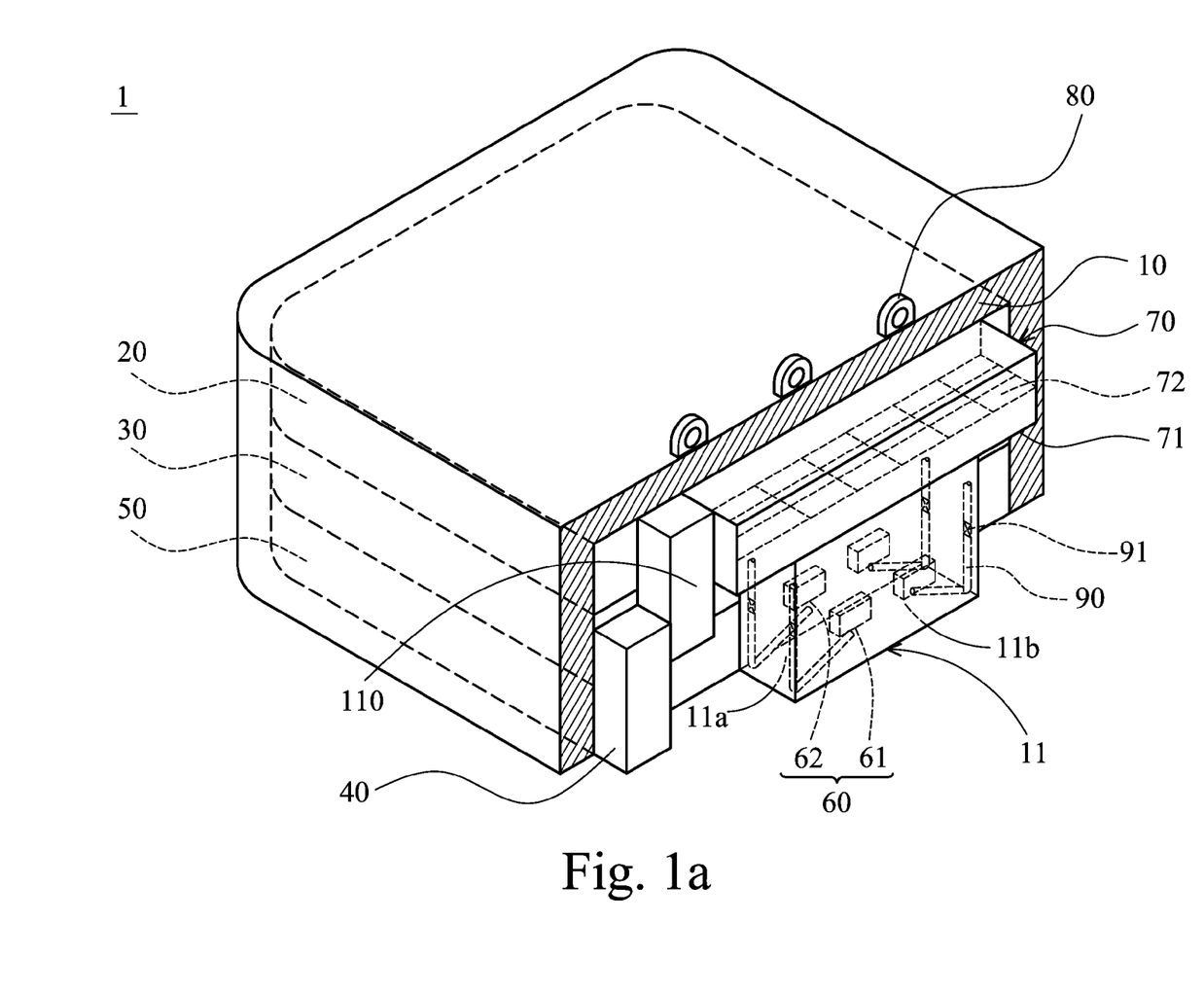
FIG. 1a is a perspective view of a cleaning apparatus according to an embodiment.
Figure 1B:
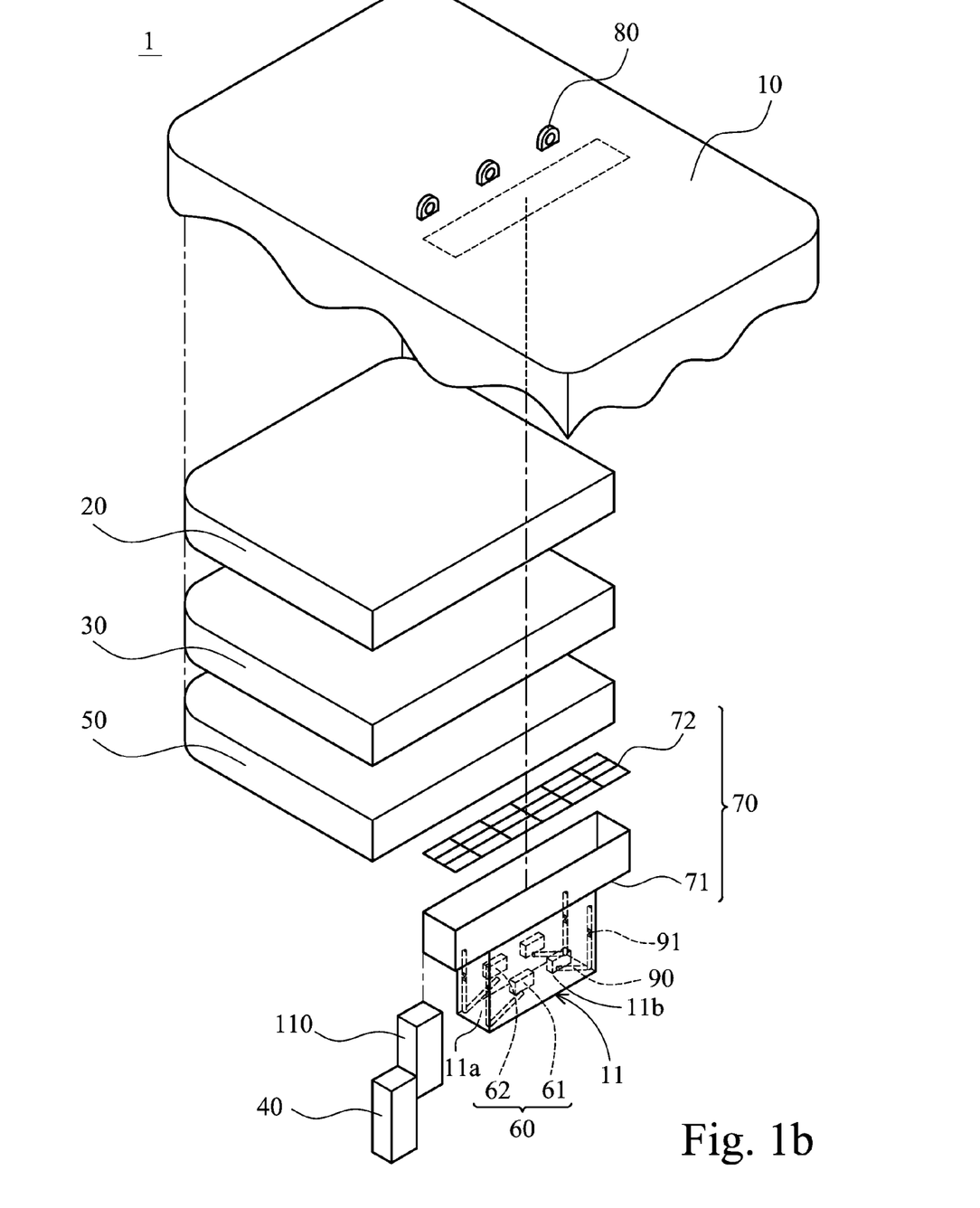
Figure 2:
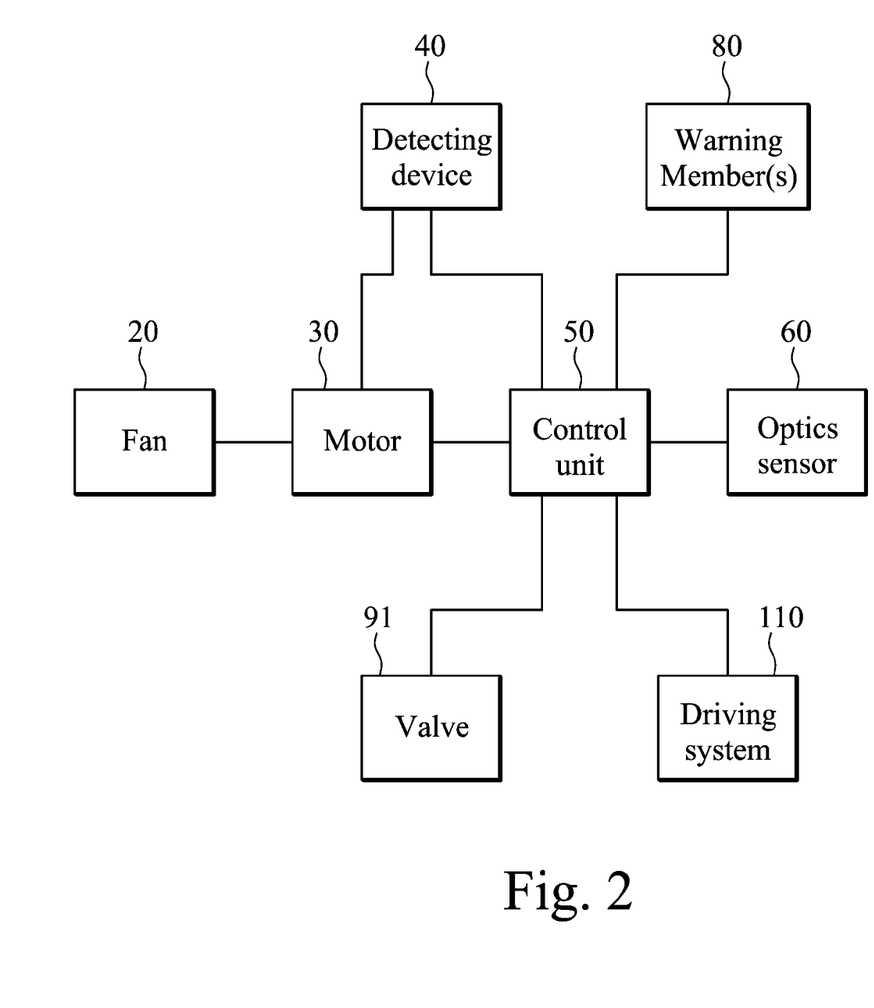
FIG. 2 is a circuit block diagram of a cleaning apparatus according to an embodiment.

Referring to FIGS. 1a, 1b and FIG. 2, cleaning apparatus 1 includes a housing 10, a fan 20, a motor 30, a detecting device 40, a control unit 50, two pairs of optics sensor 60, a dust collecting unit 70, three warning members 80, four blowing devices 90, and a driving system 110. Although, in the following illustration, cleaning apparatus 1 is sometimes referred to as an auto-cleaning device, in some embodiments, cleaning apparatus 1 can be a vacuum cleaner or an air cleaning machine. Thus, other embodiments are also within the scope of the following claims.

The housing 10 substantially encloses the fan 20, the motor 30, the detecting device 40, and the control unit 50 therein. Further, the housing 10 has an inlet 11, which has a shape of a long strip and includes a left area 11a and a right area 11b.

Referring to FIG. 1a, the motor 30 is configured to drive the fan 20 to create an air flow through the cleaning apparatus so that dust can be sucked in through the inlet 11. The motor 30 is set below the fan 20 inside the housing 10. As shown in FIG. 2, the motor 30 is coupled to the fan 20 in order to drive the fan 20.

The detecting device 40 is disposed beside the control unit 50 and the motor 30 inside the housing 10, and is electrically connected to the motor 30 and the control unit 50, respectively, in order to detect the an impendence of the motor 30. In some embodiments, if the motor 30 is a brushless motor, the detecting device 40 is integrated into the circuit of the brushless motor.

The control unit 50 is disposed below the motor 30 inside the housing 10, and is electrically connected to the motor 30, the detecting device 40, and the driving system 110, respectively, in order to control the operation of the fan 20 and the moving speed of the cleaning apparatus 1. The control unit 50 is configured to compare the detected impedance of the motor with a predetermined value and output a signal indicative of the comparison result.

The detecting device 40 of the cleaning apparatus 1 according to at least one embodiment is configured to detect an impedance of the motor 30 for measuring debris accumulation inside a dust collecting unit. The dust collecting unit could include a filter 72 and a box 71. The impedance of the motor 30 increases when the debris accumulation inside the dust collecting unit or the blockage of the air outlet and inlet increases. When the voltage of the motor 30 is fixed, it leads to the decrease of the current and increase of the resistance. The resistance of the motor 30 can be measured after the current value of the motor 30 detected by the detecting device 40. In some embodiments, the detecting device is a current detecting device that detects a current value of the fan. When the detecting device detects a current value that is below a predetermined current value, the control unit 50 may stop driving the motor 30.

Figure 3A:
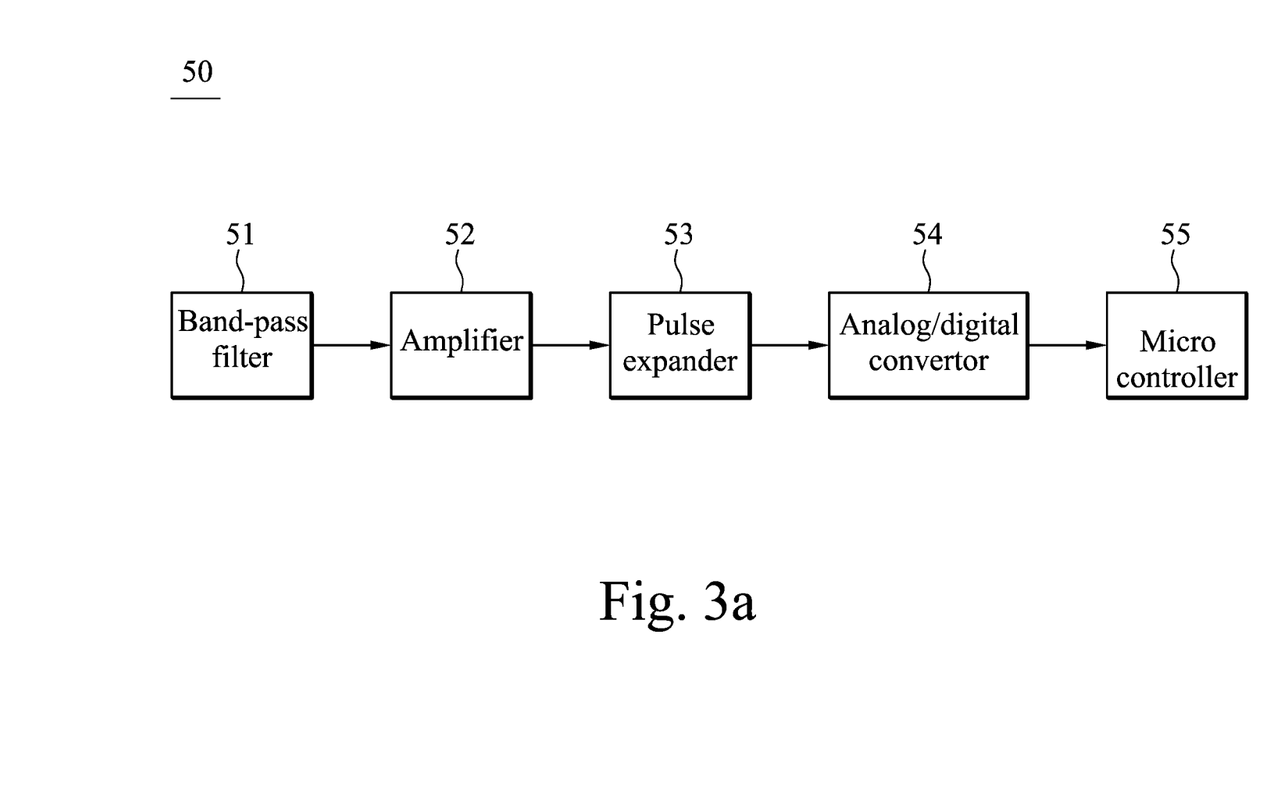
FIG. 3a is a block diagram of the control unit according to the embodiment depicted in FIG. 2.
Figure 3B:
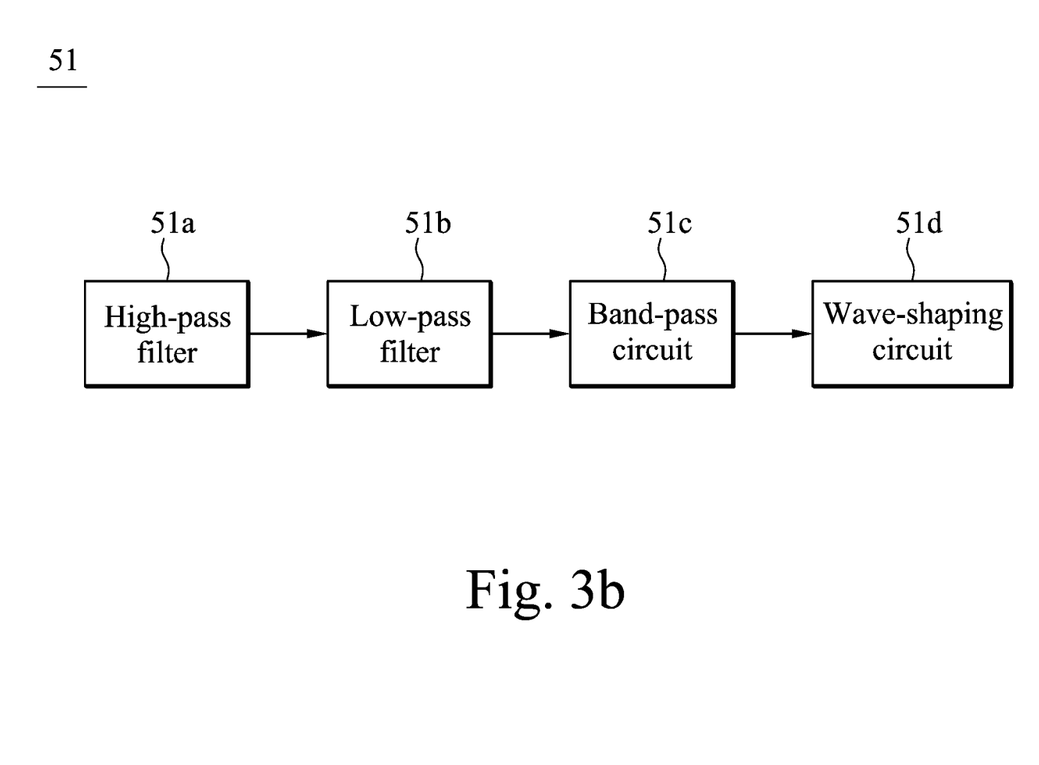

As shown in FIG. 3a, in at least one embodiment, the control unit 50 including a band-pass filter 51, an amplifier 52, a pulse expander 53, an analog/digital converter 54, and a micro controller 55. The band-pass filter 51 is a multi-level filter circuit that is configured to remove the electronic noise from other components (e.g. the motor 30). In one embodiment, as FIG. 3b shown, the band-pass filter 51 is a four-level filter circuit, including a high-pass filter 51a, a low-pass filter 51b, a band-pass circuit 51c, and a wave-shaping circuit 51d. In some embodiments, regarding the band-pass filter 51, the gain is 2±3%, the central frequency is 110 kHz±3%, the bandwidth of 3 dB is 90 kHz±3%, and an electronic bandwidth is 20 kHz~200 kHz. It should be realized that although the embodiment disclosed herein is a four-level filter circuit, it is not limited to such design. Any other circuit design is workable as long as the gain, central frequency, 3 dB bandwidth, and electronic bandwidth comply with standards previously stated.

Referring to FIG. 3a, the amplifier 52 amplifies signals from the band-pass filter 51; the pulse expander 53 adjusts the sampling frequency of signals from other components (ex: optical sensor 60); the analog/digital converter 54 performs a analog/digital conversion for signals from other components; and the micro controller 55 utilizes signals processed by the analog/digital converter 54 to control the suction and the moving speed of the cleaning apparatus 1. Furthermore, in some embodiments, it is also desirable to utilize PWM (Pulse Width Modulation) to control the suction and the moving speed stated above. When the cleaning apparatus 1 detects a rather dusty condition, it will be adjusted to have a stronger suction power and slower moving speed, therefore improving the cleaning efficiency.

Figure 3C:
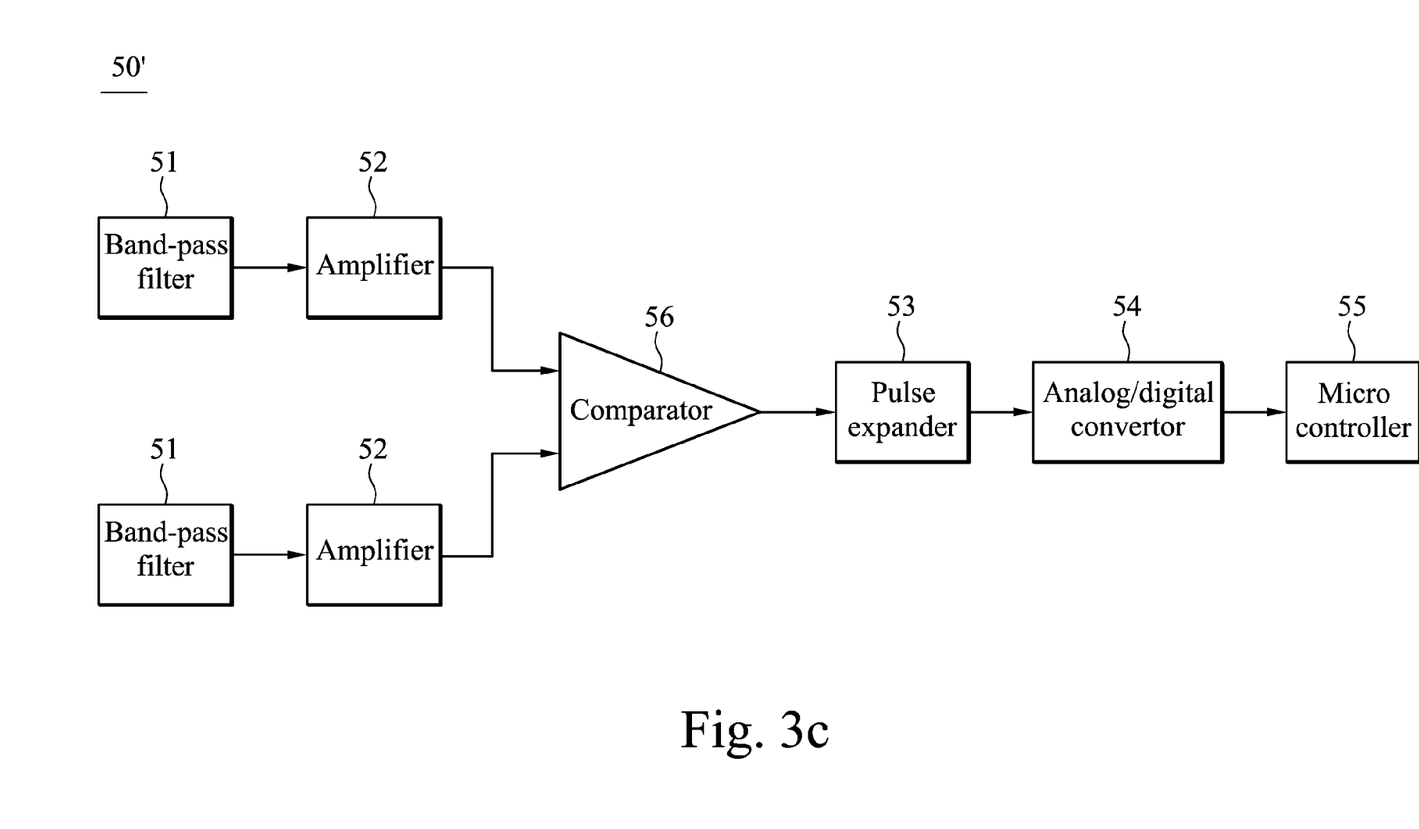
FIG. 3c is a block diagram of the control unit according to another embodiment.

It should be realized that internal configuration of control unit 50 is not limited to the way FIG. 3a shown. Any configuration accomplished substantially the same result is desirable. For example, FIG. 3c shows another example of the control unit. The control unit 50' includes two band-pass filters 51, two amplifiers 52, a pulse expander 53, an analog/digital converter 54, a micro controller 55, and a comparator 56. The difference between the control unit 50' in FIG. 3c and the control unit 50 in FIG. 3a is that the control unit 50' further includes a comparator 56. The comparator 56 compares the signal after the suction operation is commenced with the signal before the suction motion is commenced.

Referring to FIG. 1a, two pairs of optical sensors 60 are disposed inside the inlet 11 of the housing 10, in order to detect the amount of duct passing though the inlet. While the surface area of any of the two optical sensors 60 is covered by dust over a predetermined percentage (ex: over 90%), the control unit 50 ceases the motor 30 that drives the fan 20. The two optical sensors 60 are separately disposed on the left area 11a and the right area 11b inside the inlet 11. It should be realized that although the embodiment disclosed herein utilizes two optical sensors, the number of optical sensor is not limited to two, and it's also desirable to change the number of optical sensors used.

Figure 1C:
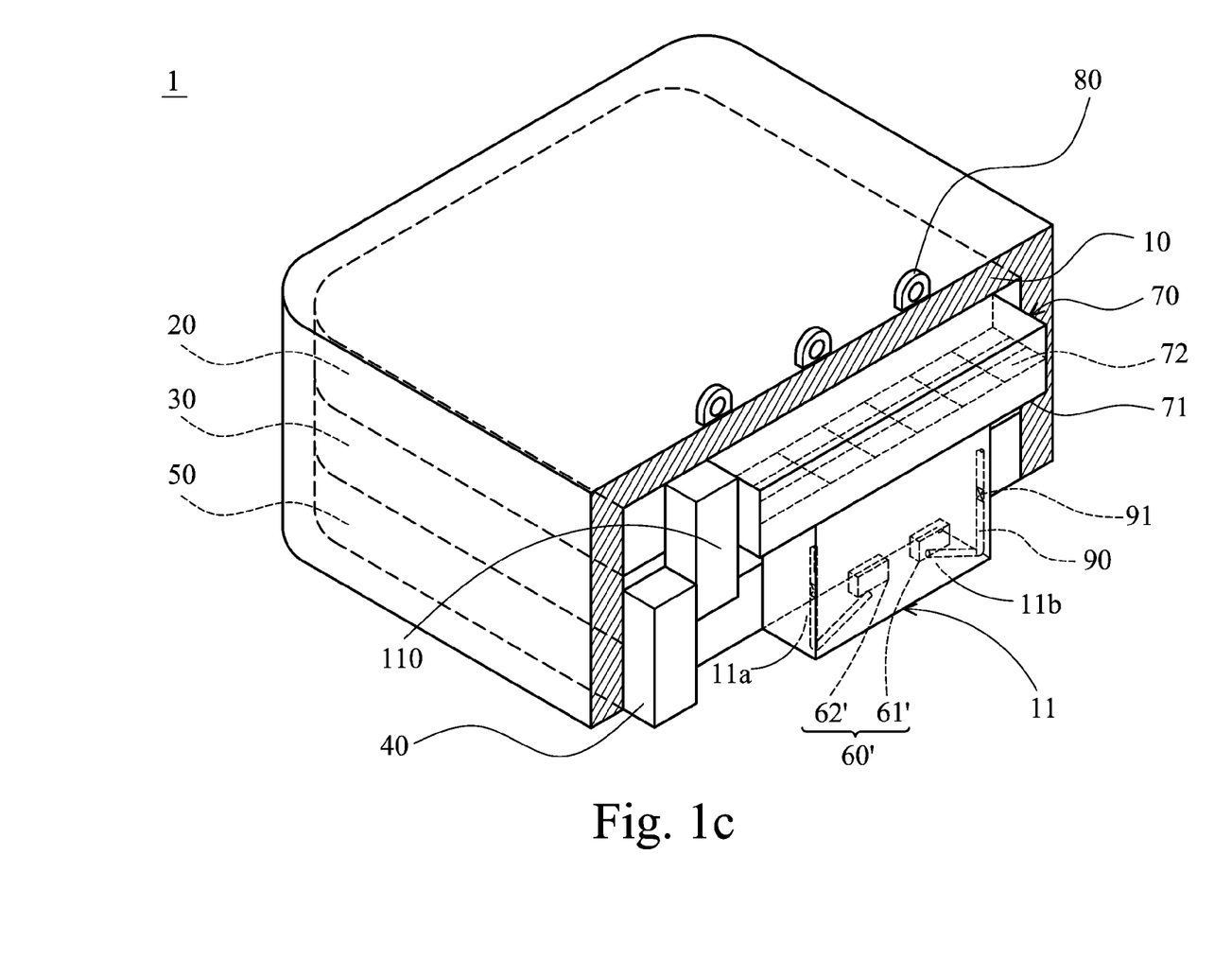
FIG. 1c is a perspective view of a cleaning apparatus according to another embodiment.
Figure 1D:
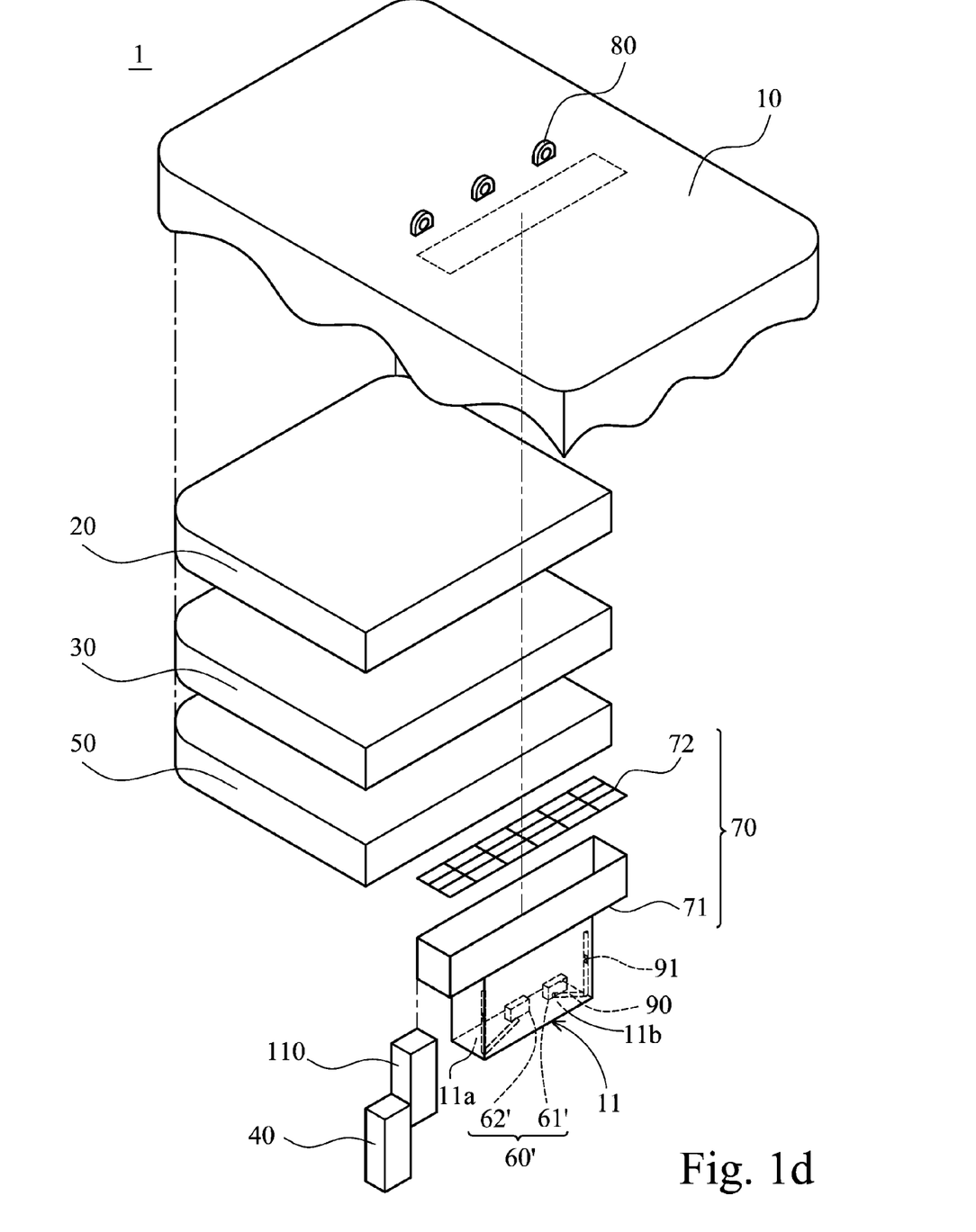
FIG. 1d is an explosive view of a cleaning apparatus according to the embodiment depicted in FIG. 1c.
Figure 4:
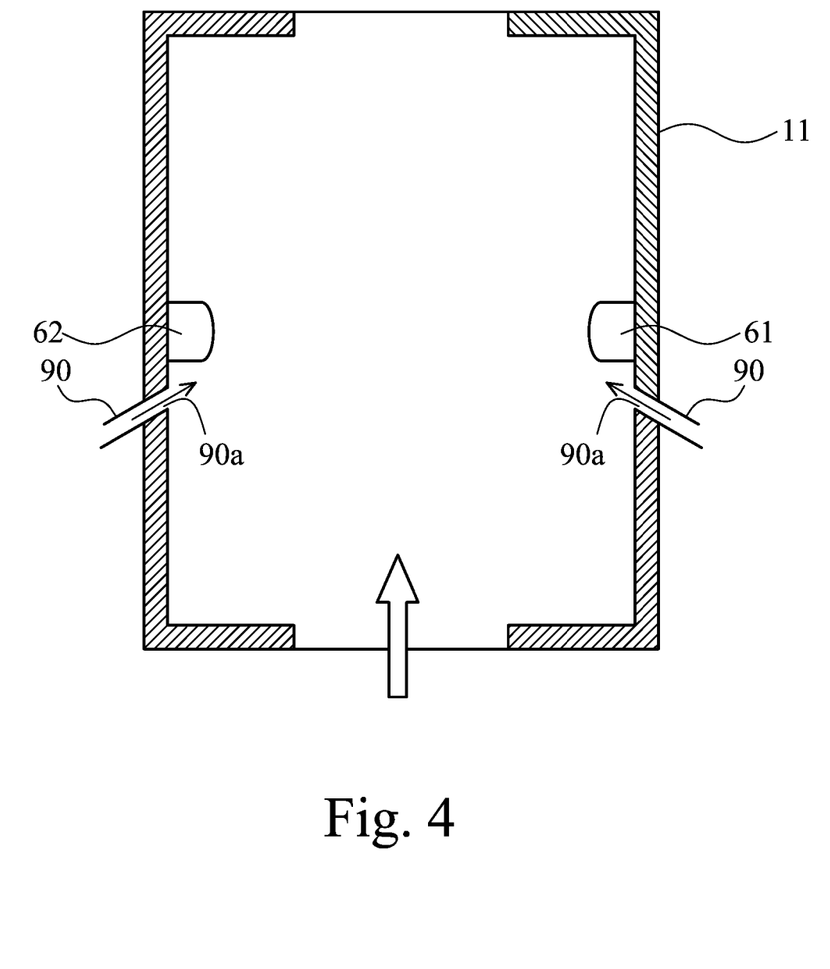
FIG. 4 is a cross-sectional view of an intake of the cleaning apparatus according to an embodiment.

As FIG. 4 shown, each optical sensor 60 comprises a transmitter 61 and a receiver 62, wherein the transmitter 61 and the receiver 62 are placed facing each other inside the inlet 11. It is realized that the location of transmitter 61 and receiver 62 is not limited to what figures illustrated. Referring FIG. 1c and FIG. 1d, in some embodiments, the transmitter 61 and receiver 62 are disposed in a manner that they both face the same direction. In that case, the receiver 62 receives signals from the transmitter 61 by reflection.

Referring FIG. 1a, the dust collecting unit 70, which is positioned in a path of the air flow to trap dust from air inhaled by to the fan 20, comprises a box 71 and a filter 72. When the control unit 50 ceases the motor 30 that drives the fan 20, the dust collecting unit 70 is configured to be cleaned up. That is, the box 71 is cleaned and/or the filter 72 is replaced by another one.

Referring FIG. 2 is a circuit block diagram of the cleaning apparatus. There are three warning members 80 disposed on the housing 10 and electrically connected to the control unit 50. The warning member 80 is activated (e.g. switched on) by the control unit 50 when the signal indicates that the impedance of the motor is higher than the predetermined value. In some embodiments, three warning members 80 may be light emitting diodes respectively and can emit light when switched on by the control unit 50. In some other embodiments, the warning member 80 can be buzzers, indicators, or other devices according to various applications. Also, although only three warning members 80 are depicted for an exemplary embodiment, the number of the warning members 80 can be more or less than three.

FIG. 4 is a cross-sectional view of an intake of the cleaning apparatus according to an embodiment. In some embodiments, there are two blowing devices 90 for directing exhaust air from the fan 20 to a sensing surface of the at least one optical sensor (not shown in figures) to blow dust off said sensing surface for preventing the optical sensor 60 from being affected by the dust coverage. Each blowing device contains one air outlet 90a. The two air outlets 90a respectively located under the transmitter 61 and the receiver 62. The two blowing devices 90 are separately connecting to the air outlet (not shown in figures) of the fan 20. The a portion of air-exhaust of the fan 20 is guided to and blows through the air outlet 90a to the transmitter 61 and the receiver 62 for cooling the transmitter 61 and/or the receiver 62 and reducing the coverage of the dust. Each of the blowing devices 90 includes a valve 91 as depicted in FIG. 1. The valve 91 electrically connected with the control unit 50 to control the exhaust air flowing through the blowing device 90. The air outlet 90a can be located under the transmitter 61 and the receiver 62 in this exemplary embodiment of FIG. 4. The air outlet 90a can also be located on the side part of the transmitter 61 and the receiver 62. The location of air outlet 90a can be adjusted as long as the exhaust air of the air outlet 90a can blow to the transmitter 61 and the receiver 62.

The driving system 110 for moving the auto-cleaning device is disposed on the housing 10, connected to the fan 20 and the motor 30 in the way as depicted in FIG. 1a, and electrically connected with the control unit 50 in the way as depicted in FIG. 2. Note that the arrangement of every element in the housing are not limited to these embodiments depicted by the figures.

Figure 5:
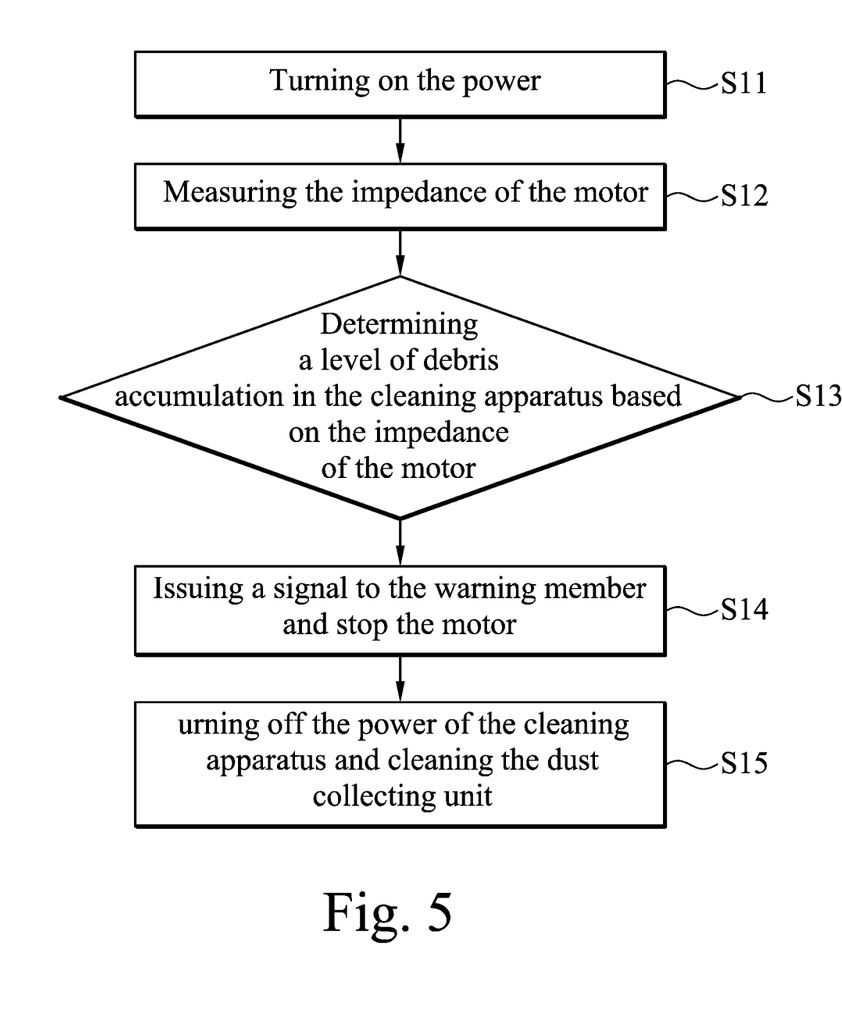
FIG. 5 is a flow chart of a detecting method of a cleaning apparatus according to an embodiment.

Referring to FIG. 5, it is a flowchart of a detecting method of the cleaning apparatus. The step of method comprises: turning on the power of the cleaning apparatus 1 (S11), measuring the impedance of the motor 30 by the detecting device 40 (S12), determining a level of debris accumulation in the cleaning apparatus 1 based on the impedance of the motor 30 (S13). When the level of debris accumulation exceeds a predetermined value, the process proceeds to Step S14. Then, a signal indicative of the level of debris accumulation exceeding a predetermined value is issued (in one or more embodiments to the warning member 80 such as light emitting diodes or buzzers), and stop the motor 30 (S14). Then, the power of the cleaning apparatus 1 is turned off and the dust collecting unit 70 is cleaned (S15).

In one embodiment, Step 4 (S14) is to issue a signal when the level of debris accumulation reaches 80% of the space inside the box 71. The predetermined percentage value of the space inside the box 71 can be adjusted according to various applications.

In one or more embodiments, to decide when to clean the dust collecting unit 70 by using the impedance value of the motor 30 can improve the efficiency of the cleaning apparatus 1.

There are three warning members 80 are disposed on the housing 10, and electrical connected with the control unit 50. When the control unit 50 determines that motor 30 for the fan 20 need to be stopped, the control unit 50 activates one or more warning members 80. In some embodiments, the warning members 80 are light-emitting diodes. When the control unit 50 activates one or more warning members 80, the light-emitting diodes (i.e. the warning members 80 being activated) emit light. Although only three warning members 80 are depicted in the exemplary embodiment, in some other embodiments, there can be more or less than three warning members 80 disposed on the housing 10. Further, the warning members 80 disclosed in the exemplary embodiment are light-emitting diodes. However, in some other embodiments, the warning members 80 can be light-emitting diodes, buzzers, other indictors, and/or combination thereof.

Figure 6:
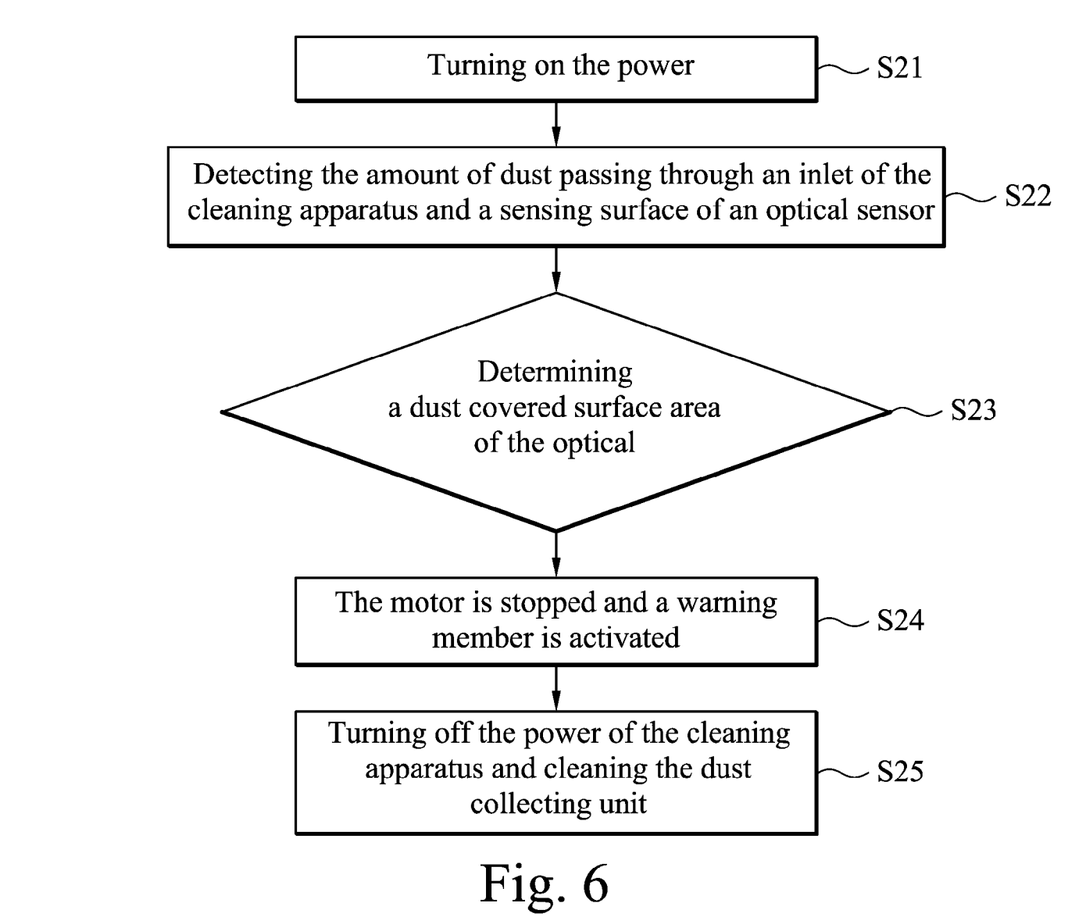
FIG. 6 is a flow chart of a detecting method of a cleaning apparatus according to another embodiment.

FIG. 6 is a flowchart of an embodiment of a detecting method in a cleaning apparatus. The detecting method comprises some steps as follows. First, power the cleaning apparatus 1 on in step S21. Next, in step S22, detect the amount of dust passing through an inlet 11 of the cleaning apparatus 1 and a sensing surface of an optical sensor 60 by the optical sensor 60. After that, in step S23, determine a dust covered surface area of the optical sensor 60. In detail, optical sensor 60 senses the status of the sensing surface. When a percentage of the sensing surface which dust covered exceed a predetermined value, such as 90% in some embodiments, the optical sensor 60 outputs a sensing signal to the control unit 50, then go to step S24. In an embodiment, the sensing surface may separate to several equal grids. By counting the number of the grids which dust covered on the sensing surface, it may obtain the percentage to determine a dust or garbage covered surface area of the optical sensor. In some embodiments, a cleaning operation of the cleaning apparatus is controlled based on the determined dust covered surface area. In step S24, when the control unit 50 receives the sensing signal, the motor 30 is stopped and a warning member 80 is activated. Finally, power off the cleaning apparatus 1 and clean a dust collecting unit 70 of the cleaning apparatus 1 in step S25.

Before the step S23, in some embodiments, a blowing device 90 can be activated and used to blow exhaust air of the fan 20 at the sensing surface of the optical sensor 60 before said determining the dust covered surface area to decrease the amount of dust or garbage covered on the sensing surface of the optical sensor 60. It may prevent the sensitivity of the optical sensor 60 from degrading. In addition, in at least one embodiment, the predetermined value is 90%, but the predetermined value may change in various applications. It is not limited hereto.

The detecting method in a cleaning apparatus which said before may determine when to clean the dust collecting unit 70 of the cleaning apparatus 1 by detecting status of the sensing surface of the optical sensor 60. It may increase the efficiency of the cleaning apparatus 1 when the cleaning apparatus 1 is working.

Figure 7:
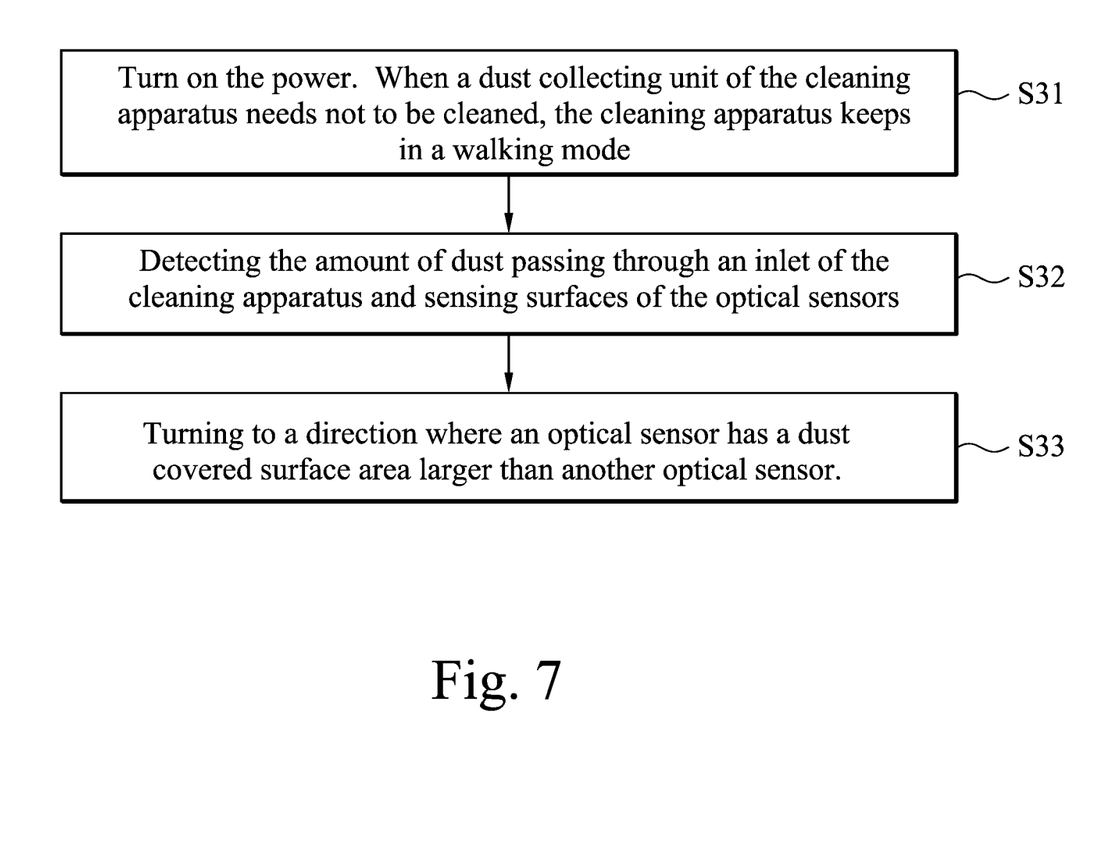
FIG. 7 is a flow chart of a detecting method of a cleaning apparatus according to yet another embodiment.

FIG. 7 is a flowchart of another embodiment of a detecting method of a cleaning apparatus. In an embodiment, the detecting method may apply to an auto-cleaning device. The auto-cleaning device comprises multiple optical sensors arranged at different locations in the inlet for detecting the sensing surface at said different locations. Take FIG. 1c and FIG. 1d for example, there are two optical sensors 62' and 61' arranged at a left area 11a and a right area 11b of the inlet, respectively, and a cleaning operation of the cleaning apparatus 1 is controlled based on the determined dust covered surface areas received from said optical sensors 60'. The detecting method comprises some steps as follows. First, in step S31, power the cleaning apparatus 1 on. When a dust collecting unit 70 of the cleaning apparatus 1 needs not to be cleaned, the cleaning apparatus 1 remains in a walking mode. Next, in step S32, detect the amount of dust passing through an inlet 11 of the cleaning apparatus 1 and sensing surfaces of the optical sensors 62' and 61' by the optical sensors 60'. Then, compare with the determined dust covered surface areas received from the optical sensors. In an embodiment, the cleaning apparatus 1 turns to a direction where an optical sensor has a dust covered surface area larger than another optical sensor in step S33. For example, when the determined dust covered surface area of the optical sensor 62' at the left area 11a larger then the determined dust covered surface area of the optical sensor 61' at the right area 11*b*, the cleaning apparatus 1 turns left. On the contrary, when the determined dust covered surface area of the optical sensor 61' at the right area 11*b* larger then the determined dust covered surface area of the optical sensor 62' at the right area 11*a*, cleaning apparatus 1 turns right. In addition, the cleaning operation of the cleaning apparatus 1 further adjusts at least one suction power and/or a moving speed of the cleaning apparatus 1 in said direction.

Before the step S32, a blowing device 90 may be activated to blow exhaust air of the fan 20 at the sensing surface of the optical sensors 60'. It may prevent the sensitivity of the optical sensors 60' from degrading. Furthermore, in some embodiments, when the cleaning apparatus 1 turns to said direction, a turning radius of the cleaning apparatus 1 is equal to a length of the inlet 11.

By the detecting method in a cleaning apparatus set forth above, the cleaning apparatus may decide which side is dirtier based on determined dust covered surface area of the optical sensors 62' and 61' at the left area 11*a* and the right area 11*b* respectively. It may increase the cleaning efficiency of the cleaning apparatus 1.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for debris detection in a cleaning apparatus, said method comprising:
    measuring an impedance of a motor of a fan of the cleaning apparatus;
    determining a level of debris accumulation in the cleaning apparatus based on the impedance of the motor;
    issuing a signal indicative of the level of debris accumulation exceeding a predetermined value;
    determining a dust covered surface area of an optical sensor, wherein the optical sensor is disposed inside an inlet of the cleaning apparatus;
    controlling a cleaning operation of the cleaning apparatus based on the determined dust covered surface area; and
    blowing exhaust air of the fan toward the sensing surface of the optical sensor before determining the dust covered surface area.

2. The method as claimed in claim 1, further comprising: stopping the motor in response to said signal.

3. The method as claimed in claim 1, further comprising: arranging multiple optical sensors at different locations in the inlet for detecting the sensing surface at said different locations;
    wherein the cleaning operation of the cleaning apparatus is controlled based on the determined dust covered surface areas received from said optical sensors.

4. The method as claimed in claim 3, wherein said controlling comprises: turning the cleaning apparatus to a direction of the optical sensor with the determined dust covered surface areas larger than those determined by the other optical sensors.

5. The method as claimed in claim 4, wherein said controlling further comprises:
    adjusting at least one of suction power and a moving speed of the cleaning apparatus in said direction.

6. The method as claimed in claim 4, wherein a turning radius of the cleaning apparatus is equal to a length of the inlet.

7. The method as claimed in claim 1, wherein measuring the impedance of the motor comprises measuring a current supplied to the motor, the method further comprising:
    turning off the motor if the measured current decreases below a predetermined current value.

8. A method for debris detection in a cleaning apparatus, said method comprising:
    measuring an impedance of a motor of a fan of the cleaning apparatus, by measuring a current supplied to the motor;
    determining a level of debris accumulation in the cleaning apparatus based on the impedance of the motor;
    issuing a signal indicative of the level of debris accumulation exceeding a predetermined value;
    turning off the motor if the measured current decreases below a predetermined current value;
    determining a dust covered surface area of an optical sensor, wherein the optical sensor is disposed inside an inlet of the cleaning apparatus; and
    blowing exhaust air of the fan toward the sensing surface of the optical sensor before determining the dust covered surface area.

9. A method for debris detection in a cleaning apparatus, said method comprising:
    determining a level of debris accumulation in the cleaning apparatus based on a measured impedance of the motor;
    issuing a signal indicative of the level of debris accumulation exceeding a predetermined value;
    determining a dust covered surface area of an optical sensor, wherein the optical sensor is disposed inside an inlet of the cleaning apparatus;
    blowing exhaust air of the fan toward a sensing surface of the optical sensor, prior to the exhaust air exiting the cleaning apparatus; and
    controlling a cleaning operation of the cleaning apparatus based on the determined dust covered surface area.

* * * * *